(12) United States Patent
Bercoff et al.

(10) Patent No.: US 10,795,007 B2
(45) Date of Patent: Oct. 6, 2020

(54) METHOD AND A DEVICE FOR IMAGING A VISCO-ELASTIC MEDIUM

(75) Inventors: Jérémy Bercoff, Aix en Provence (FR); David Savery, Cabries (FR); Claude Cohen-Bacrie, Ventrabren (FR); Jacques Souquet, Puyricard (FR)

(73) Assignee: Super Sonic Imagine (FR)

(*) Notice: Subject to any disclaimer, the term of this patent is extended or adjusted under 35 U.S.C. 154(b) by 2121 days.

(21) Appl. No.: 12/294,898

(22) PCT Filed: Mar. 22, 2007

(86) PCT No.: PCT/EP2007/052767
§ 371 (c)(1),
(2), (4) Date: Sep. 26, 2008

(87) PCT Pub. No.: WO2007/110375
PCT Pub. Date: Oct. 4, 2007

(65) Prior Publication Data
US 2010/0168566 A1 Jul. 1, 2010

Related U.S. Application Data

(60) Provisional application No. 60/810,637, filed on Jun. 5, 2006.

(30) Foreign Application Priority Data

Mar. 29, 2006 (FR) ..................... 06 02709

(51) Int. Cl.
*G01S 7/52* (2006.01)
*G01S 15/89* (2006.01)
(Continued)

(52) U.S. Cl.
CPC ........ *G01S 7/52036* (2013.01); *A61B 5/0051* (2013.01); *A61B 8/08* (2013.01);
(Continued)

(58) Field of Classification Search
USPC ............ 600/370, 438, 454–456; 73/570, 573
See application file for complete search history.

(56) References Cited

U.S. PATENT DOCUMENTS

| 4,043,181 A | 8/1977 | Nigam | |
|---|---|---|---|
| 5,606,971 A * | 3/1997 | Sarvazyan | .................. 600/438 |

(Continued)

FOREIGN PATENT DOCUMENTS

| EP | 1800603 | 6/2007 |
|---|---|---|
| FR | 2844058 A1 | 3/2004 |

(Continued)

OTHER PUBLICATIONS

Nightingale et al. ("On the feasibility of remote palpation using acoustic radiation force"; J. Acoust. Soc. Am. 110 (1), Jul. 2001).*

(Continued)

*Primary Examiner* — Oommen Jacob
*Assistant Examiner* — Shahdeep Mohammed (57) ABSTRACT

The invention relates to a method and a device for imaging a visco-elastic medium (2). The method comprises an excitation step during which an internal mechanical stress is generated in an excitation zone [A] and an imaging step of acquiring signals during the movements generated by the mechanical stress in the visco-elastic medium (2) in response to the internal mechanical stress in an imaging zone [B] that includes the excitation zone [A]. According to the invention, the method further comprises a step of calculating a quantitative index [Cij] associated with the rheological properties of the visco-elastic medium (2) at at least one point [Bij] of the imaging zone situated at a given depth outside the excitation zone [A].

16 Claims, 2 Drawing Sheets (51) Int. Cl.
*A61B 8/08* (2006.01)
*A61B 5/00* (2006.01)
*A61N 7/00* (2006.01)

(52) U.S. Cl.
CPC ............ *A61B 8/0825* (2013.01); *A61B 8/485* (2013.01); *G01S 7/52042* (2013.01); *G01S 15/8961* (2013.01); *G01S 15/8977* (2013.01); *A61B 8/0833* (2013.01); *A61N 7/00* (2013.01)

(56) References Cited

U.S. PATENT DOCUMENTS

| | | | |
|---|---|---|---|
| 5,810,731 | A | 9/1998 | Sarvazyan |
| 6,113,543 | A * | 9/2000 | Bonnefous .................... 600/438 |
| 6,135,957 | A * | 10/2000 | Cohen-Bacrie et al. ..... 600/438 |
| 6,511,427 | B1 * | 1/2003 | Sliwa et al. ................. 600/438 |
| 6,558,324 | B1 | 5/2003 | Von Behren et al. |
| 7,112,173 | B1 * | 9/2006 | Kantorovich ........ A61B 8/0875 600/438 |
| 7,632,232 | B2 * | 12/2009 | Lewandowski et al. ..... 600/438 |
| 7,753,847 | B2 * | 7/2010 | Greenleaf et al. ........... 600/438 |
| 7,892,188 | B2 * | 2/2011 | Walker et al. ................ 600/587 |
| 2004/0167403 | A1 | 8/2004 | Nightingale |
| 2005/0004466 | A1 * | 1/2005 | Hynynen et al. ............. 600/449 |
| 2005/0015009 | A1 * | 1/2005 | Mourad et al. ............... 600/438 |
| 2005/0101867 | A1 * | 5/2005 | Johnson .................. A61B 8/14 600/459 |
| 2005/0154306 | A1 * | 7/2005 | Burcher et al. .............. 600/447 |
| 2005/0252295 | A1 * | 11/2005 | Fink et al. ...................... 73/603 |
| 2005/0288580 | A1 * | 12/2005 | Lagrange et al. ............ 600/437 |
| 2006/0074315 | A1 * | 4/2006 | Liang et al. .................. 600/450 |
| 2007/0016037 | A1 * | 1/2007 | Houle et al. .................. 600/438 |
| 2007/0112267 | A1 * | 5/2007 | Matsumura et al. ......... 600/437 |

FOREIGN PATENT DOCUMENTS

| | | |
|---|---|---|
| JP | 2005533320 | 11/2005 |
| WO | WO2004010380 | 1/2004 |

OTHER PUBLICATIONS

Bercoff J et al. "Supersonic Shear Imaging: A New Technique for Soft Tissue Elasticity Mapping", IEEE Transactions on Ultrasonics, Ferroelectrics and Frequency Control, vol. 51, No. 4, Apr. 2004, pp. 396-409.

Bercoff J et al. "Study of Viscous and Elastic Properties of Soft Tissues Using Supersonic Shear Imaging", 2003 IEEE Ultrasonics Symposium Proceedings, vol. 1 of 2, Oct. 2003.

Nightingale et al. "Acoustic remote palpation: initial in vivo results", Ultrasonics Symposium, vol. 2, Oct. 2000, pp. 1553-1558.

International Search Report for International Application No. PCT/EP07/052767.

Office Action for related Canadian Patent Application No. 2,647,283 dated Nov. 12, 2013.

Office Action for related European Patent Application No. 07727241.7 dated Apr. 21, 2009.

Office Action for related European Patent Application No. 07727241.7 dated Feb. 2, 2010.

Office Action for related Japanese Patent Application No. 2009-502039 dated Dec. 6, 2011.

* cited by examiner

METHOD AND A DEVICE FOR IMAGING A VISCO-ELASTIC MEDIUM

CROSS-REFERENCE TO RELATED APPLICATIONS

This national stage application claims the benefit under 35 U.S.C. §371 of International Application No. PCT/EP2007/052767 filed on Mar. 22, 2007, entitled A METHOD AND A DEVICE FOR IMAGING A VISCO-ELASTIC MEDIUM, which in turn takes its priority from French Application No. 06 02709 filed on Mar. 29, 2006 and U.S. Provisional Application No. 60/810,637 filed on Jun. 5, 2006, and all of whose entire disclosures are incorporated by reference herein.

BACKGROUND OF THE INVENTION

Field of Invention

The present invention relates to the general field of methods and devices for imaging a visco-elastic medium and including studying movements that exist in the visco-elastic medium. More particularly, the invention relates to methods comprising an excitation step during which an internal mechanical stress is generated in an excitation zone, followed by a step of imaging by acquiring signals during the movements generated in the visco-elastic medium in response to the internal mechanical stress in an imaging zone which includes the excitation zone.

In a particularly advantageous application, the invention relates to imaging the visco-elastic properties of human organs. In this medical application, the invention serves in particular to detect the presence of a liquid zone in an organ such as the breast, the liver, the ovary, etc. and to characterize that zone.

Echographic examination of the breast already makes it possible to deduce certain characteristics of observed lesions from information about the morphology and the echographic texture of those lesions. In particular, it is possible to distinguish between a cystic lesion and a solid mass on the basis of echogenicity values that reveal the acoustic specificity of liquid. A typical cyst appears on the echographic image as a zone of geometrically regular shape that does not generate echoes, given that the liquid filling the cyst contains few diffusers, whereas the echogenicity of tissue beyond the cyst appears to be clearly enhanced since the incident beam is attenuated more weakly in the cyst than in tissue.

It is also possible to estimate the risk of a solid lesion being malignant as a function of its morphology. An image having sharp outlines with few lobes and a major axis parallel to the skin is more likely to be associated with a lesion that is benign. Conversely, an image that is irregular, e.g. being star-shaped, with outlines that are poorly defined, and with strong posterior shadowing is very likely to be malign.

Unfortunately, those morphological criteria can be insufficient since they are not completely reliable, particularly with small lesions. This lack of specificity has led to new echographic tools emerging that give quantifiable functional information that is more correlated with pathological states.

For example there are elastographic techniques that seek to measure the mechanical properties of tissue for the purpose of characterizing lesions more finely and systematically.

The rheology of the medium can also be analyzed in order to distinguish solid and liquid natures, and it is known in particular to generate radiation pressure in a well defined zone of interest in order to generate therein, if the zone is liquid, a flow of that liquid which can then be imaged by echography.

The image obtained reveals movements in the zone of interest. When movement is observed on the resulting image, then the presence of liquid has been detected.

Such a method of detecting the presence of a liquid merely by detecting movement leads to lesions being classified in a manner that is not very robust, in particular with cysts that are complex, that are often echogenic with content that is viscous, as are encountered in about 50% of cases. The movement induced in the radiation pressure zone in a cyst of that type remains very similar to the mechanical response of a visco-elastic solid. The presence or absence of movement is then not a distinguishing criterion. However, it is specifically with cysts of that type that the morphological criteria given by echography usually turn out to be insufficient.

Furthermore, known methods are capable only of testing a particular zone of the medium as selected by the user. The method is specific and it is not practical to envisage implementing the known method continuously while imaging a medium.

Finally, the known method serves only to detect the presence of liquid, and does not provide any graduation in the rheology of lesions. Amongst other things, these lesions may be cysts that are viscous, milky, calcified, hemorrhagic, or indeed made up of sediments, and they can thus present rheological properties that are distinct and varied.

OBJECT AND SUMMARY OF THE INVENTION

The main aim of the present invention is thus to mitigate such drawbacks by proposing an elastographic technique that makes it possible in particular within a single lesion, to distinguish between liquid and solid components, the invention consisting in a method as described in the introduction and further comprising a step of calculating a quantitative index associated with the rheological properties of the visco-elastic medium at at least one point of the imaging zone situated at a given depth outside the excitation zone, said quantitative index being representative of a comparison between signals acquired during the movements generated in response to the mechanical stress at at least one point of the excitation zone situated at the given depth, and signals acquired during the movements generated in response to the mechanical stress at at least the point of the imaging zone situated outside the excitation zone.

Such a method is based on characterizing relative movements of different zones of the visco-elastic medium, the zones being distinguished by the way in which they respond to the mechanical stress. The method proposes systematically calculating a quantitative index to reveal the presence or absence of a propagating mechanical wave in the medium outside the excitation zone. The method of the present invention thus makes it possible to observe a broad zone of the medium, e.g. by giving a map of the quantitative index at a plurality of points. The quantitative index is advantageously a similarity index.

The signals acquired for calculating the quantitative index are preferably a displacement field, or a movement field, or ultrasound noise or "speckle". Acquiring such fields is well known to the person skilled in the art.

The method of the invention makes it possible to identify solid and liquid zones on the basis of the wave propagation criterion, which is a robust physical criterion. The invention then enables rheology to the characterized over the entire imaging zone. With the invention, all of the characterizations are performed without prior knowledge of the zone in which the medium is imaged.

In an advantageous implementation, the step of comparing the acquired signals comprises comparing time variations and/or amplitude variations in the acquired signals.

Advantageously, the calculation step comprises calculating the maximum of a correlation function between the signals acquired for two points under consideration, the quantitative index being a function of said maximum.

According to another particular characteristic of the invention, the internal mechanical stress is a mechanical vibration generated by ultrasound radiation pressure.

It is then the presence or the absence of propagation of a shear wave generated by said mechanical vibration that enables solids and liquids to be distinguished. It should be observed that generating such a shear wave is advantageous since the method of the invention is then performed in parallel with measuring the elasticity of the visco-elastic medium using methods that are known, e.g. from patent WO2004/0210838. In addition, generating such a shear wave makes it possible to apply mechanical excitation to a medium in depth, and thus to probe rheology deeply within organs. This imparts another advantage to this type of stimulation.

In an advantageous application, the excitation step is coupled with treatment. The stress is then advantageously generated by a beam used for therapeutic purposes, e.g. a focused ultrasound wave beam.

Furthermore, in the invention, the excitation that enables movement to be generated in the medium may be result of a variety of mechanisms, including in particular one or more biological mechanisms, or indeed external vibration at low frequency. According to the invention, such mechanisms need to generate internal mechanical stress that is localized in an excitation zone.

In a particular feature of the invention, the imaging step comprises a sub-step of emitting ultrasound waves into the imaging zone at a repetition frequency that is sufficient for measuring the dynamics of the movements generated by the internal mechanical stress; a sub-step of detecting and recording the ultrasound echoes generated within the medium as acquired signals; and a sub-step of estimating movement from the detected echoes for at least two successive emissions of ultrasound waves and from the ultrasound wave emission frequency, the quantitative index being calculated from said estimated movement.

In known manner, the ultrasound waves generated during this imaging step are reflected by tissue diffusers on the lines of propagation of the excitation wave. With such a feature, it is possible in particular to use the same array of transducers for exciting and for imaging the medium.

In an advantageous implementation, at least two "directional" quantitative indices are calculated for two points situated at the same given depth outside the excitation zone, one on either side of the excitation zone, said quantitative indices being representative of two comparisons between signals acquired during the movements generated in response to the mechanical stress at at least one point of the excitation zone situated at the given depth, and signals acquired during the movements generated in response to the mechanical stress at at least the two points of the imaging zone situated outside the excitation zone.

Such a feature makes it possible to specify the properties of the medium at a given depth on either side of a given excitation zone. It is then possible, when the excitation zone is localized at an interface between two zones of different echogenicities, to reveal different visco-elastic characteristics on either side of the interface.

In a particular implementation of the invention, the quantitative index is calculated at the boundary of a region of the medium defined by echography in order to test the permanent or temporary character thereof in the surrounding medium.

Such an implementation makes it possible to test for possible sliding of a solid lesion within tissue. This fixed or rolling aspect of the lesion within the surrounding tissue is likewise an important criterion for characterizing the lesion.

Advantageously, a secondary quantitative index associated with a point of the excitation zone at a given depth is calculated as a function of spatial variations of the quantitative indices of points situated outside the excitation zone along a line at said given depth.

Such a characteristic makes it possible to determine regions having different visco-elastic properties along said line, for example in order to determine the extent of a zone of tissue necrosis or a zone of complete coagulation induced by High Intensity Focused Ultrasound "HIFU" while performing HIFU treatment on a lesion.

Advantageously, a secondary quantitative index is calculated for a plurality of points at different depths in the excitation zone.

Such a characteristic makes it possible to determine the visco-elastic properties of the medium as a function of depth. This can make it possible in particular to define the outlines of a zone containing liquid.

Advantageously, the quantitative index or the secondary quantitative index calculation is reiterated at different instants.

Such a characteristic makes it possible to track variation in the visco-elastic properties of the medium as a function of time. In particular, this can make it possible to track variation in the size of a necrosis induced by HIFU or indeed by radio-frequency treatment as a function of treatment time.

Advantageously, a "time" quantitative index is calculated as a function of time variations in a quantitative index.

Such a time index can be calculated for a simple quantitative index and also for a secondary quantitative index.

Advantageously, the method can be reiterated by moving the excitation zone so as to measure quantitative indices throughout a zone of interest in the visco-elastic medium.

Advantageously, the method includes a step of constructing an echographic image of the visco-elastic medium; and the method further comprises a step of displaying a quantitative index or a magnitude derived from said index as brightness or color values on the echographic image that is obtained.

In an advantageous implementation, knowledge of the quantitative index (indices) is used to calculate parameters for a treatment and its progress by tracking modification of the medium, in particular the size of induced coagulation or tissue necrosis. By way of example, the treatment performed may be High Intensity Focused Ultrasound treatment (HIFU) or treatment by radio frequencies.

It is also possible to use the quantitative index (indices) for calculating parameters of other types of localized treatment, in particular radio-frequency treatment.

The invention also provides a device for imaging a visco-elastic medium, the device comprising excitation means for generating internal mechanical stress in an excitation zone and imaging means for acquiring signals to image movements generated by the mechanical stress in the visco-elastic medium in response to the internal mechanical stress in an imaging zone that includes the excitation zone. The device of the invention further comprises calculation means for calculating a quantitative index associated with the rheological properties of the visco-elastic medium at at least one point situated at a given depth outside the excitation zone, said quantitative index being representative of a comparison between signals acquired during the movements generated in response to the mechanical stress at at least one point of the excitation zone situated at the given depth, and signals acquired during the movements generated in response to the mechanical stress at at least the point of the imaging zone situated outside the excitation zone.

Advantageously, the excitation means are an array of transducers that can also serve as imaging means.

In a preferred implementation, the various steps of the method are determined by computer program instructions.

Consequently, the invention also provides a computer program on a data medium, the program being suitable for being implemented in an imaging device and including instructions adapted to implement the following steps : excitation during which an internal mechanical stress is generated in an excitation zone; imaging the medium by acquiring signals during the movements generated by the mechanical stress in the visco-elastic medium in response to the internal mechanical stress in an imaging zone that includes the excitation zone; and calculating a quantitative similarity index associated with the rheological properties of the visco-elastic medium on the basis of a comparison between signals acquired during the movements generated in response to the mechanical stress at at least one point of the excitation zone, and signals acquired during the movements generated in response to the mechanical stress at at least the point of the imaging zone situated outside the excitation zone.

The program can use any programming language and it may be in the form of source code, object code, or code intermediate between source code and object code, such as a partially-compiled form, or in any other desirable form.

The invention also provides a data medium readable by an imaging device and including computer program instructions as specified above.

The data medium may be any kind of entity or device capable of storing the program. For example, the medium may comprise storage means such Read-Only Memory (ROM), e.g. CD ROM or a microelectronic circuit ROM, or indeed magnetic recording means, e.g. a floppy disk or a hard disk.

Furthermore, the data medium may be a transmission medium such as an electrical or optical signal, that can be conveyed via an electrical or optical cable, by radio, or by other means. In particular, the program of the invention may be downloaded from a network of the Internet type.

Alternatively, the data medium may be an integrated circuit in which the program is incorporated, the circuit being adapted to execute or to be used in the execution of the method in question.

BRIEF DESCRIPTION OF THE DRAWINGS

Other characteristics and advantages of the present invention appear from the following description made with reference to the accompanying drawings which show an embodiment having no limiting character. In the figures.

DETAILED DESCRIPTION OF AN EMBODIMENT

Figure 1:
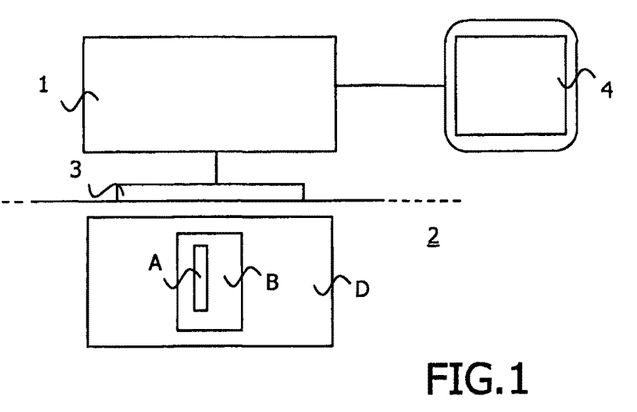
FIG. 1 is a diagrammatic representation of the use of a device of the invention.

FIG. 1 is a diagrammatic representation of an imaging device 1 in accordance with the invention for imaging a visco-elastic medium 2. In an advantageous application, the medium 2 is biological tissue, for example a human organ or portion of an organ, such as the breast.

The device 1 is connected to at least one ultrasound probe 3. Such a probe 3 may comprise a single element or a one-dimensional or a two-dimensional array of transducers. While the device of the invention is in use for observing the medium 2, the probe 3 is in contact with the medium 2.

The device 1 includes electronic means for controlling the emission of compression waves, e.g. ultrasound waves, by the probe 3.

The visco-elastic medium 2 diffuses such compression waves. In particular, ultrasound compression waves can propagate therein, thus enabling an echographic image to be made.

Advantageously, the device 1 is connected to a display module 4 enabling information extracted from the imaging data to be displayed.

Figure 2:
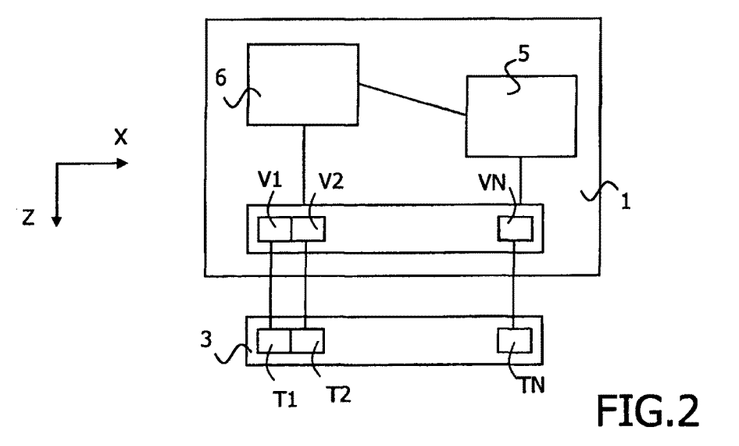
FIG. 2 is diagrammatic representation of a device of the invention.

FIG. 2 shows more precisely the device 1 and the probe 3. In the example shown in this figure, the probe 3 is a linear one-dimensional array of transducers comprising N elements [T1, T2, . . . TN], where N is equal to 128, for example. The device 1 includes a certain number of channels V, preferably N channels [V1, V2, . . . VN], i.e. 128 channels in this example, capable of controlling the transducer elements [T1, T2, . . . TN] of the probe 3 independently.

A software module 5 serves to control the electronic channels [V1, V2, . . . VN], in order to implement excitation and imaging sequences, and also to alternate these sequences.

A memory module 6 serves to record the back-scattered ultrasound signals that are received during imaging sequences.

According to the invention, in order to observe the rheology of the medium 2, the device 1 is programmed to implement the various steps of the method of the invention.

The first step of the method consists in mechanical excitation generating internal mechanical stress within the medium 2. Excitation signals are thus sent to the transducer elements over the electronic channels, themselves controlled by the software module 5.

The internal mechanical stress is advantageously generated by successively emitting one or more ultrasound compression waves, that are optionally focused, using the set of independent transducer elements [T1, 12, . . . TN], or using a single transducer element.

By way of example, the excitation step can be performed by focusing a sound beam of sufficient energy to excite the tissue at one or more depths in succession.

Advantageously, the device 1 is capable of increasing the energy of these waves, either by increasing the amplitude of the pressure field, or by lengthening the emitted wavetrain. In the intended applications, the length of the wavetrain advantageously lies in the range 1 microsecond (µs) to 10,000 µs.

The frequency of the excitation ultrasound waves advantageously lies in the range 0.1 megahertz (MHz) to 50 MHz. Furthermore, it is possible to use time coding of the excitation signals in order to improve their penetration.

Figure 3:
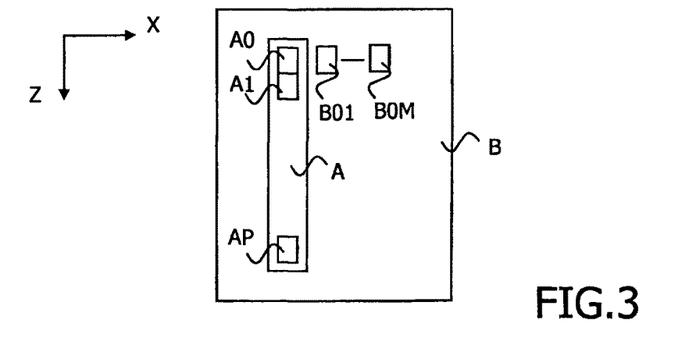
FIG. 3 shows a particular implementation of the invention in a visco-elastic medium.

FIG. 3 shows the mechanism of the invention in a medium 2. In this figure, a plurality of waves are emitted that are focused on points Ai situated at different depths. An "excitation" zone A covering the focusing points Ai of the waves is thus insonified. The waves used are of sufficient energy to cause tissue to be moved, principally in the Z direction, thereby generating a shear wave. For example, a wavetrain is used of a length that may lie in the range 1 µs to 10,000 µs, with the number of beams used lying in the range 1 to 50, and with these various excitation sequences being emitted at a repetition rate oscillating in the range 10 hertz (Hz) to 20,000 Hz. The insonified zone A is then excited by ultrasound radiation pressure.

The compression waves can also be focused on at least two different locations, simultaneously or in alternation. The excitation zone A is in any event a concatenation of a set of insonified points. It should also be observed that using waves that are unfocused or little focused can be advantageous for covering an excitation zone that is broad and spread out.

The second step of the method of the invention is an imaging step, during which ultrasound shots are emitted in succession so as to illuminate an "imaging" zone B of the medium 2 that contains the excitation zone A. Preferably, the same array of transducers [T1, T2, . . . TN] is used as for the excitation step, possibly using excitation frequencies or voltages different from those that were used for the excitation sequence.

The use of a second array of transducers or of other elements included in the first array, or indeed the use of a single-element transducer is also entirely conceivable as an alternative. This makes it possible, in particular, to proceed with the imaging step in parallel with the excitation step.

The firing rate during the imaging step must be quite high in order to observe the propagation of a shear wave or a flow. In general, this corresponds to firing rates lying in the range 0.1 Hz to 20,000 Hz.

The acoustic illumination of the medium 2 during the imaging step may be performed using ultrasound waves that are focused or unfocused.

During this imaging step, reflecting particles present in the zone B of the medium 2 reflect the ultrasound waves. These reflections give rise to ultrasound echoes. The back-scattered signals corresponding to these ultrasound echoes are then detected by the array of transducers [T1, T2, . . . TN] and recorded in the memory module 6.

It is then possible to observe the effects of movements on the echographic image. More particularly, from the acquired ultrasound echoes, an estimate of movements in the medium serves to quantify the mechanical response of the visco-elastic medium to the internal excitation stress. To make this estimate of movement, the back-scattered signals corresponding to a given set of reflecting particles or diffusers are compared with one another in order to estimate a displacement of said set of diffusers relative to an initial or preceding position.

The estimated displacement may be axial or vectorial. When the displacement is estimated relative to one of the preceding shots on the basis of the delays in the arrival times at the transducer elements [T1, T2, . . . TN], and the ultrasound propagation speed is assumed to be constant and known, a displacement speed is obtained.

Conventional methods of estimating movement known to the person skilled in the art can be used in this situation. For example, it is possible to maximize cross-correlation functions, a method of the frequency type such as estimating phase shifts, or indeed a Doppler method for estimating speed. Vectorial approaches can also be envisaged such as a vectorial Doppler method or using light flux.

These estimation methods are implemented within a software module 5 which processes data stored in the memory module 6.

For example, the software module 5 is such that channel formation is implemented so as to calculate a succession of echographic images of the imaging zone B and then calculate a movement estimate from said images using one-dimensional or vector algorithms known to the person skilled in the art.

The movement field calculated while estimating the movement induced by the excitation internal mechanical stress may be an absolute displacement field or a relative displacement field, i.e. a speed.

Advantageously, to estimate displacement, it can be advantageous to perform a preliminary step of imaging the medium 2 prior to the excitation. Such a step consists in emitting at least one compression ultrasound wave and in receiving the reflected echoes in order to set up a reference set of echoes.

The following step of the method of the invention is a step of calculating a quantitative index for analyzing the rheology of the medium. It consists in estimating coherence of the displacement fields that result from the excitation between at least one point of the excitation zone A and one point of the imaging zone B outside the zone A.

FIG. 3 illustrates implementing such a calculation in an observation zone B of a visco-elastic medium 2. For local quantification of mechanical behavior about the point A0 belonging to the excitation zone A, the invention makes use of an estimate of the movement at said point A0 and an estimate of the movement at at least one point B01 of the imaging zone situated outside the excitation zone A. It is particularly useful to quantify the variations in time of the movements.

The point B01 is preferably located at short distance from the point A0, e.g. 0.5 millimeters (mm) laterally therefrom, in particular in order to determine the fluid or solid nature of the zone A0.

In practice, the term "point" is used to designate a small physical zone of the medium 2 that surrounds a geometrical point of the medium 2. The size of such a physical zone may be variable in order to achieve a compromise between estimation robustness and processing time. The displacement in the zones can be summarized by an arithmetic mean over the pixels contained in these critical zones, for example.

When a plurality of pixels or a plurality of units for which a displacement is calculated correspond to a given physical zone of the medium surrounding a point, the quantitative index, e.g. calculated from a correlation coefficient, is calculated as a mean of quantitative indices calculated for each pair of pixels or units in the zones A and B, e.g. the mean of the correlation coefficients calculated for each pair of pixels in the zones A and B.

According to the invention, a comparison is made between the variations in time of the displacements, or in similar manner, the variations in time of the speeds, as observed in the various zones surrounding the points A0 and B01, and a quantitative index associated with the visco-elastic nature of the medium 2 is deduced therefrom.

This quantitative index preferably characterizes the spatial coherence of the displacement fields at the two points. Spatial coherence means the similarity that does or does not exist between the displacement fields acquired at different points. This coherence relates to the amplitude of the acquired signals and/or to the variations in time of these signals. The quantitative index may, in particular, be referred to as a "similarity" index. In order to quantify the amplitude similarity and the time variation similarity, the index may be constituted in particular by a maximum correlation coefficient between the displacement signal at A0 and the displacement signal at B01.

Figure 4A:
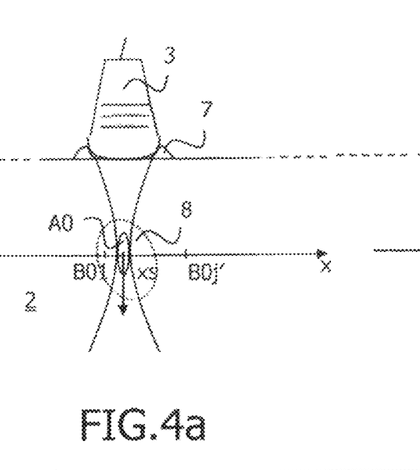
FIGS. 4a and 4b are diagrammatic representations of an imaging method of the invention being implemented in a zone including a liquid and in a zone that is entirely solid.
Figure 4B:
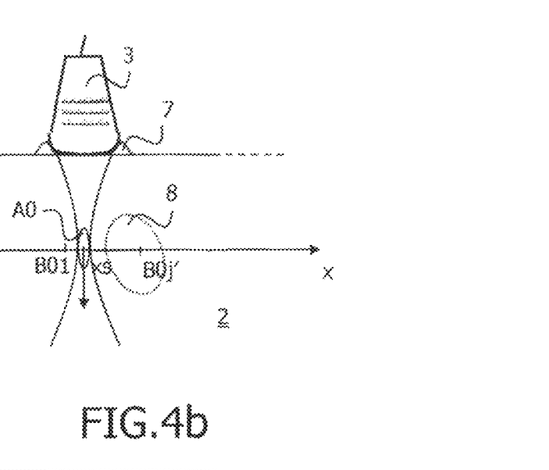

FIGS. 4a and 4b show the method being implemented in a medium 2 that includes a pocket of liquid 8, respectively when the point A0 of the excitation zone is situated in the pocket of liquid 8, and when the point A0 of the excitation zone is situated outside the pocket of liquid 8.

The quantitative index is a maximum correlation coefficient calculated using the following formula:

$$C01(x) = \frac{\max_{\Delta t}\left(\int s(x_s, t + \Delta t)s(x_s + x, t)dt\right)}{\sqrt{(\int s(x_s, t)s(x_s, t)dt) \times (\int s(x_s + x, t)s(x_s + x, t)dt)}}$$

where t scans a time interval, s is the field under investigation which may, in particular, be a speed or displacement field or indeed an ultrasound speckle intensity field, x is the abscissa of the point B01 located at the same depth as the point A0, and xs is the abscissa of the point A0. Such a coefficient is representative of a comparison between the variations in time of the signals acquired for the points A0 and B01 during the movements of the medium.

Such a maximum correlation coefficient can be calculated between the displacement or speed fields that result from a time average of the displacement or speed fields at the points A0 and B01.

Other types of quantitative index can be calculated in order to quantify the similarity between the displacement signals at A0 and at B01. In particular, this can involve different distances such as a p-norm, the Euclidean norm (p=2), entropy criteria such as Kuliback divergence, etc., between raw or amplitude-normalized signals or between signals that are optionally shifted, or indeed by calculating a maximum of the cross-correlation function.

Advantageously, as shown in FIG. 3, a plurality of points B0j, for j=1 to M, are observed that are situated at the same depth as the point A0 and that are at various distances from the point A0. Once more, the variations in time of the displacements, or in similar manner, the variations in time of the speeds, as observed in the various zones surrounding the points A0 and B0j are compared spatially and a quantitative index associated with the visco-elastic nature of the medium 2 is deduced for each point B0j. Thus, a plurality of points at increasing distances from A0 are analyzed after a given excitation.

Advantageously, and as shown in FIGS. 4a and 4b, at least two directional quantitative indices C01 and C0j' are calculated, one on either side of the excitation zone for two points B01 and B0j', each situated on one side of the excitation zone.

The invention then makes it possible in particular to detect and characterize interfaces, since an interface between two media of different visco-elastic characteristics can be characterized by analyzing the mechanical responses in and on either side of the excitation zone A. A large difference of value between two directional quantitative indices on either side of a given excitation zone is representative of the presence of an interface, i.e. a sudden change in mechanical properties in the vicinity of the excitation zone A.

Figure 5:
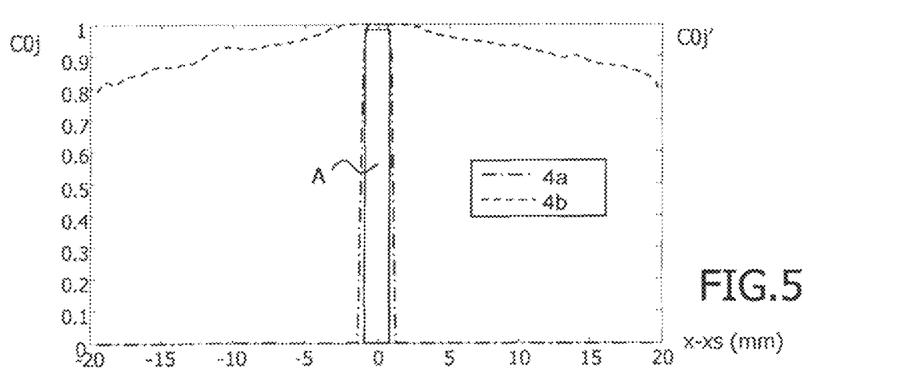
FIG. 5 is a graph showing the correlation coefficient obtained for the two circumstances shown in FIGS. 4a and 4b.

FIG. 5 shows the values of the directional quantitative indices constituted by a maximum correlation coefficient as described above and obtained during the imaging performed as shown in FIGS. 4a and 4b for a plurality of points B0j and B0j' having abscissa co-ordinates x up to 20 mm on either side of the excitation zone A. In FIG. 4a, the curve that is obtained shows decorrelation of the field under study outside the excitation zone A to which the point A0 belongs. A curve of such appearance corresponds to the presence of liquid at the point A0.

In contrast, for FIG. 4b, the resulting curve shows a correlation maximum that decreases slightly for increasing abscissa co-ordinates x of the points B0j and B0j'.

It can be advantageous to determine the point B0j for which a quantitative index is at a maximum. The point A0 can then be associated with such an index, which, for example, may be a maximum of the maximum correlation coefficient between the displacement signal at A0 and the displacement signals at the points B0j){B01 . . . B0M}.

In particular, the variation in the quantitative index with distance A0B0j can then also advantageously give rise to a secondary quantitative index to characterize the rheology of the visco-elastic medium 2. This secondary quantitative index describes the decrease in the quantitative index with distance from A0. Such a secondary quantitative index associated with the point A0 is advantageously calculated from the spatial variations of the previously calculated quantitative indices on the line at the same depth as the point A0.

For example, it is possible to estimate the gradient of the quantitative index at the depth of the point A0, to calculate the distance corresponding to the quantitative index dropping by n %, e.g. 90%, to calculate the concavity of the quantitative index, or some other property associated with the spatial second derivatives of the quantitative index, etc., each of these magnitudes possibly constituting a secondary quantitative index associated with a given depth of the excitation zone A.

Such a calculation can then be reiterated several times over so as to calculate a secondary quantitative index at a plurality of points at different depths and so as to calculate a map of this secondary quantitative index in the excitation zone A. In parallel, a map of the quantitative index in the imaging zone B can also be drawn up.

As shown in FIG. 3, the excitation zone A is then subdivided into P+1 points Ai={A0 . . . AP} in the Z direction. For each measurement point Ai, a set of M points Bij with j≥1 is defined in the imaging zone B on at least one side of the excitation zone A.

A maximum correlation coefficient Cij between at least one speed or displacement time field of the point Ai and at least one speed or displacement time field of the point Bij is calculated for all i≤P and for all j≤M.

Iteration then consists in calculating a secondary quantitative index at different points A0 . . . AP of the excitation zone A, with P≤0, from the quantitative similarity indices calculated for the points Bij. The secondary quantitative index calculated at Ai is defined, for example, as the maximum value of the derivative of the correlation coefficients Cij relative to j.

The coefficients Cij can also be calculated between speed or displacement fields resulting from a time average of speed or displacement fields at a plurality of points in the zones A and B involved.

Calculation of the secondary quantitative indices is repeated for each i, i≤P, thereby covering all of the points Ai of the excitation zone A.

Thereafter, the excitation zone A can be moved in a succession of excitation shots. By performing a plurality of alternating excitation and imaging sequences, and by moving the excitation and Imaging zones A and B, e.g. laterally in the imaged medium, it is possible to displace A in depth or in azimuth so as to cover an extended zone D as shown in FIG. 1.

Figure 6:
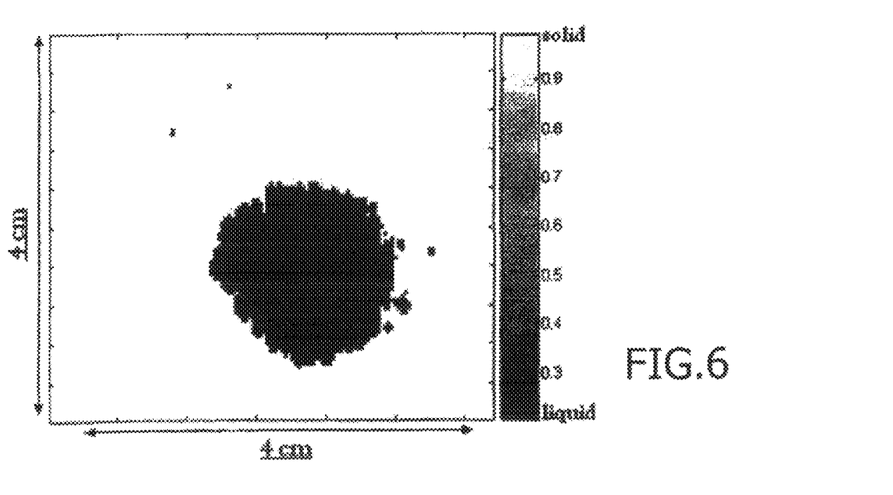
FIG. 6 shows an example of a display of a quantitative index in accordance with the invention.

It is then possible to give a binary value to each excited point A of the medium 2, e.g. by using a threshold for the secondary quantitative index, and to display this value by using a color code or a display code. An example of such a display is given in FIG. 6 where the black zone corresponds to detecting the pocket of liquid 8 as shown in FIG. 4.

Advantageously, two "directional" secondary quantitative indices can be defined around the excitation zone, one being the maximum of the derivative Cij relative to j, where j corresponds to the points Bij situated on one side of Ai, the other being the maximum of the derivative Cij' relative to j, where j corresponds to the points Bij' on the other side of Ai. Once more, such secondary quantitative indices serve to reveal the presence of an interface when they are very different on either side of the excitation zone.

It is also possible to calculate a "time" quantitative index from the time variations of the quantitative indices calculated successively for a given pair [Ai; Bij]. Such a secondary index serves in particular to give additional information about the relaxation time of the medium, which quantity is associated with the viscosity of the medium.

It should be observed that it is also possible to use time variations of a secondary index as previously calculated. Such a calculation at a plurality of depths can be envisaged in the invention.

It is also possible to calculate a secondary quantitative index from spatial variations as a function of the depths of quantitative indices calculated for a set of points A0 . . . AP paired with a set of points Bij=B0j to BPj, situated at the points A0 . . . AP.

On the same lines, it is also possible to use spatial variations as a function of the depth of a secondary quantitative index as previously calculated. Once more, calculation is performed for a plurality of depths.

Such a secondary quantitative index can serve in particular to give an indication about the extent in depth of a lesion by making it possible in particular to test for the presence of a deep interface.

Knowledge of the above-described quantitative indices makes it possible to analyze the behavior of the medium 2 both inside and outside the excitation zone A and makes it possible to deduce particular visco-elastic behaviors.

A clear distinction between liquid behavior and solid behavior can be achieved on the basis that the movement induced in a fluid is a flow that remains confined in the mechanical excitation zone A and possibly in its very close vicinity. In contrast, in a solid, the excitation creates a propagating shear wave which extends the mechanical response spatially well away from the source.

On the basis of the calculated quantitative indices given by way of example, a large value for quantitative similarity indices is representative of strong correlation between fields in and outside the source, indicating the presence of a propagating shear wave that is characteristic of a visco-elastic solid. Conversely, small values for the quantitative similarity indices are more representative of a viscous liquid.

Thus, a correlation coefficient close to 1 obtained regardless of the position of the point Bij means that an elastic wave is propagating with little attenuation and that the medium is solid.

In a solid that is more viscous, attenuation will cause the correlation coefficients to decrease progressively with distance AiBij.

Conversely, in a fluid, the correlation coefficient drops very quickly with the distance AiBij. This is due to the fact that the excitation at Ai and the liquid flows at Bij are of very different kinds.

Thus, by calculating a quantitative index at a plurality of pairs of points [Ai; Bij], it is possible to detect spatial variations in the quantitative indices that are characteristic of visco-elastic properties changing suddenly or otherwise in two dimensions of the imaged medium. For example, in the particular application to detecting mammary lesions, a clearly limited lesion, i.e. having well defined outlines, is often benign and will present spatial variations in the quantitative index that are very different from those of infiltrating malign lesions that are much less clearly defined. Such a determination of the mechanical characteristics of the interfaces between healthy tissue and lesions enables them to be characterized.

Determining a quantitative index in accordance with the invention can also serve to quantify the viscosity of a fluid, in particular the movement of the fluid spreading in the direction that extends transversally to the source and that attenuates in the axial direction to a greater extent with increasing viscosity of the fluid.

For a visco-elastic solid, the spatial variations of the time mechanical response quantified by the quantitative indices calculated for various pairs of points Ai and Bij in the medium to a propagating shear wave are greater with increasing viscosity and decreasing elasticity.

Since the quantitative index gives an estimate of spatial consistency between two points in a shear field, it is a pertinent indicator of the relaxation time of the medium and also an estimator of the quality with which elasticity is measured. Thus, by relying on the quality criterion that the quantitative index can represent, a quantitative elasticity estimate may optionally be made in parallel, e.g. using the method described in patent WO2004/0210838.

The entire method of the invention can advantageously be repeated continuously while imaging a medium so as to periodically refresh the calculated quantitative index map(s). In particular, it is possible to calculate quantitative indices at discrete instants, e.g. for the purpose of tracking variation in a zone being necrosed while the medium 2 is being subjected to HIFU treatment. Tracking quantitative indices in this way can be used for implementing automatic control of the method of treating the medium.

Advantageously, an image of a quantitative index in the imaging zone, or of a magnitude associated therewith, is displayed. For this purpose, it is possible to use an appropriate color code. Such a display can be implemented in superposition on a standard echographic image, or it may be juxtaposed. The display may be graduated, thus, for example, enabling viscosity to be evaluated, or it may be binary, thus making it possible to distinguish liquid regions from solid regions. Thus, for example, a quantitative index value may be associated with a pixel color value, and a map of the quantitative similarity index of the zone D may be created and displayed on the display module 4.

What is claimed is:

1. A method of two or three-dimensional imaging of a visco-elastic medium with a device comprising an ultrasonic probe comprising at least a first transducer element and a second transducer element, the method comprising the following steps:

exciting, by at least the first transducer element, the medium at a given depth within an excitation zone in the depth of the medium, which generates an internal mechanical stress that is localized within the medium in the excitation zone, the internal mechanical stress being of sufficient energy to cause tissue to be moved, generating a shear wave;

imaging, by at least the second transducer element, an imaging zone of the medium that comprises the excitation zone;

acquiring displacement signals during movements generated by the internal mechanical stress in the visco-elastic medium in response to the internal mechanical stress, the movements resulting from the propagation of the shear wave, the displacement signals including a first displacement signal and a second displacement signal, wherein:

the first displacement signal corresponds to a first point in the excitation zone in response to the internal mechanical stress, and the second displacement signal corresponds to a second point in the imaging zone at the same depth as the first point but outside the excitation zone, and calculating, using a microprocessor, a quantitative index associated with rheological properties of the visco-elastic medium, the quantitative index being representative of a comparison between at least one of time variations and amplitude variations of the first and second displacement signals.

2. A method according to claim 1 wherein the calculation step comprises calculating a maximum of a correlation function of the acquired signals for the two points under consideration the quantitative index being a function of this maximum.

3. A method according to claim 1, wherein the internal mechanical stress is mechanical vibration generated by ultrasound radiation pressure.

4. A method according to claim 1, wherein the imaging step comprises:

a sub-step of emitting ultrasound waves into the imaging zone at a repetition frequency that is sufficient for measuring a dynamics of the movements generated by the internal mechanical stress;

a sub-step of detecting and recording the ultrasound echoes generated within the medium as acquired signals; and a sub-step of estimating movement from the detected echoes for at least two successive emissions of ultrasound waves and from the ultrasound wave emission frequency, the quantitative index being calculated from the estimated movement.

5. A method according to claim 1, wherein at least two directional similarity quantitative indices are calculated for two points situated at the same given depth outside the excitation zone, one on either side of the excitation zone, the quantitative indices being representative of two comparisons between signals acquired during the movements generated in response to the mechanical stress at at least one point of the excitation zone situated at the given depth, and signals acquired during the movements generated in response to the mechanical stress at at least the two points of the imaging zone situated outside the excitation zone.

6. A method according to claim 1, wherein the quantitative index is calculated at a boundary of a region of the medium defined by echography in order to test a permanent or temporary character thereof in the surrounding medium.

7. A method according to claim 1, wherein a time quantitative index is calculated as a function of time variations in the quantitative index.

8. A method according to claim 1, further comprising constructing an echographic image of the visco-elastic medium, and displaying the quantitative index or a magnitude derived from the index as brightness or color values on the echographic image that is obtained.

9. A method according to claim 1, further comprising calculating parameters for a treatment and its progress by tracking modification of the medium based on the quantitative index.

10. A computer program product including non-transitory instructions for executing the steps of the imaging method according to claim 1, when the program is executed on a computer.

11. A non-transitory recording medium readable by an imaging device and having recorded thereon a computer program including instructions for executing the steps of the imaging method according to claim 1.

12. A method according to claim 1, wherein the method further comprises a step of displaying an image of the quantitative index or of a magnitude associated therewith.

13. A method according to claim 1, wherein a secondary quantitative index associated with a point of the excitation zone at a given depth is calculated as a function of spatial variations of the quantitative indices of points situated outside the excitation zone along a line at the given depth.

14. A method according to claim 13, wherein a secondary quantitative index is calculated for a plurality of points at different depths in the excitation zone.

15. A method according to claim 13, wherein the quantitative index or the secondary quantitative index calculation is reiterated at different instants.

16. A device for two or three-dimensional imaging of a visco-elastic medium, the device comprising:

an ultrasonic probe comprising at least a first transducer element and a second transducer element, the at least first transducer element being configured to excite the medium at a given depth within an excitation zone in the depth of the medium, generating an internal mechanical stress that is localized within the medium in the excitation zone, the internal mechanical stress being of sufficient energy to cause tissue to be moved, generating a shear wave; and the at least second transducer element being configured to image an imaging zone of the medium that comprises the excitation zone;

wherein at least one of the first and second transducer elements are configured to acquire displacement signals during movements generated by the internal mechanical stress in the visco-elastic medium in response to the internal mechanical stress, the movements resulting from the propagation of the shear wave, the displacement signals include a first displacement signal and a second displacement signal, wherein:

the first displacement signal corresponds to a first point in the excitation zone in response to the internal mechanical stress, and the second displacement signal corresponds to a second point in the imaging zone at the same depth as the first point but outside the excitation zone, and a microprocessor for calculating a quantitative index associated with rheological properties of the viscoelastic medium, the quantitative index being representative of a comparison between at least one of time variations and amplitude variations of the first and second displacement signals.

\* \* \* \* \*